United States Patent [19]

Fankhauser

[11] 4,453,013

[45] Jun. 5, 1984

[54] PROCESS FOR PREPARING NOVEL ACETYLENIC COMPOUNDS USEFUL AS STARTING MATERIALS FOR PREPARING AN ALICYCLIC KETONE

[75] Inventor: Peter Fankhauser, Onex, Switzerland

[73] Assignee: Firmenich, S.A., Geneva, Switzerland

[21] Appl. No.: 322,747

[22] Filed: Nov. 19, 1981

Related U.S. Application Data

[62] Division of Ser. No. 198,250, Oct. 17, 1980, Pat. No. 4,324,729.

[30] Foreign Application Priority Data

Oct. 24, 1979 [CH] Switzerland ......................... 9526/79

[51] Int. Cl.$^3$ ............................................. C07C 45/00
[52] U.S. Cl. .................................... 568/361; 549/416; 556/449; 568/591; 568/824

[58] Field of Search ...................... 568/361, 824, 591; 556/449; 549/416

[56] References Cited

U.S. PATENT DOCUMENTS 3,928,400 12/1975 Olson et al. ......................... 568/824
3,946,078 3/1976 Rautenstrauch et al. .......... 568/361

OTHER PUBLICATIONS

McOmie, Advances in Organic Chemistry, vol. 3, 1963 Edit., Raphael et al., Interscience Publishers, New York, pp. 216-219.

Primary Examiner—Nicky Chan
Attorney, Agent, or Firm—Scully, Scott, Murphy & Presser

[57] ABSTRACT

Novel acetylenic compounds useful as starting materials for the preparation of β-damascenone. Process for their preparation and use thereof.

5 Claims, No Drawings

PROCESS FOR PREPARING NOVEL ACETYLENIC COMPOUNDS USEFUL AS STARTING MATERIALS FOR PREPARING AN ALICYCLIC KETONE

CROSS REFERENCE TO RELATED APPLICATION

This application is a divisional of U.S. application Ser. No. 198,250, filed Oct. 17, 1980, and now is U.S. Pat. No. 4,324,729, issued on Apr. 13, 1982, which is hereby incorporated by reference.

SUMMARY OF THE INVENTION

The invention relates to compounds of formula

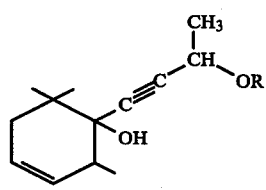 (I)

wherein symbol R represents a hydrogen atom, a trialkylsilyl radical or a group of formula

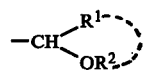 (II)

wherein, when taken separately, each of symbols $R^1$ and $R^2$ represents a lower alkyl radical or, when taken together, $R^1$ and $R^2$ represent a tetramethylene group.

The invention also relates to a process for preparing a compound of formula (I) which comprises reacting 2,6,6-trimethyl-cyclohex-3-en-1-one with an organo-metallic derivative of formula

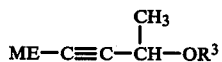 (III)

wherein symbol ME represents an alkali-metal or a halogen-magnesium radical and $R^3$ represents a trialkyl-silyl radical or a group of formula (II) as defined hereinabove, and subsequently hydrolyzing the obtained reaction product.

The invention further relates to the use of a compound of formula (I) as starting material for preparing β-damascenone, which comprises treating said compound of formula (I) with an acidic agent.

The invention finally relates to a process for preparing β-damascenone, which comprises treating 2,6,6-trimethyl-cyclohex-3-en-1-one with an organo-metallic derivative of formula (III) as defined hereinabove, subsequently hydrolyzing the obtained reaction product and finally treating the resulting product with an acidic agent.

BACKGROUND OF THE INVENTION

β-Damascenone, an alicyclic ketone having the formula

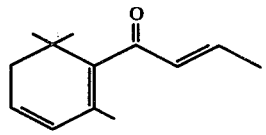

is a particularly well-appreciated fragrant and flavourant compound. The use thereof as perfuming or flavour-modifying ingredient is the object of several patents, namely U.S. Pat. No. 3,975,310, Swiss Pat. Nos. 520,479 and 509,399.

Many synthesis have been proposed in the past for preparing β-damascenone, the most interesting ones being cited hereinafter:

dehydrogenation of the corresponding cyclohexenic compound, viz. β-damascone (see Swiss Pat. No. 505,773);

treatment of 1-(2,6,6-trimethyl-1,2-epoxy-cyclohex-yl)-but-2-en-1-one with an acidic dehydrating agent (see DE-AS No. 20 65 322); and treatment of 4-(2,6,6-trimethyl-1-hydroxy-cyclohex-2-en-1-yl)-but-3-yn-2-ol with an acidic dehydrating agent (see DE-PS No. 22 42 751).

Despite of the existence of several synthetic methods, there could exist one day certain difficulties of supply of the market, mainly due to the large increase of interest shown by the perfume and flavour industry for this particularly useful ingredient.

It is therefore necessary either to improve the yield of the existing methods or to elaborate new and original syntheses, namely syntheses starting from cheaper or more accessible raw materials. The invention provides an efficient solution to this problem.

PREFERRED EMBODIMENTS OF THE INVENTION

The first step of the preparation of the acetylenic compounds of the formula (I) consists in reacting 2,6,6-trimethyl-cyclohex-3-en-1-one with an organo-metallic derivative of formula (III), according to the methods usual in the art. As organo-metallic derivatives, the sodium, potassium or lithium derivatives can be conveniently used to this end. Such a reaction is effected in the presence of an inert organic solvent, for example a hydrocarbon, hexane, an ether, diethyl ether or tetrahydrofuran e.g., an alcohol or any mixture of the above cited solvents. The organo-metallic derivatives of formula (III) wherein the symbol ME represents a halogen-magnesium radical such as MgBr, MgCl or MgI can also be conveniently used. The bromo-magnesium derivative is used preferably, in the conditions of a Grignard reaction.

As indicated above, symbol $R^3$ in formula (III) may either represent a trialkyl-silyl radical, preferably a trimethyl-silyl radical, or a group of formula

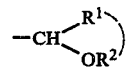 (II)

wherein, when taken separately, each of symbols $R^1$ and $R^2$ represents a lower alkyl radical, methyl, ethyl or propyl e.g.: 3-oxa-pent-2-yl ($R^1$=methyl; $R^2$=ethyl) is an example of such a radical. Symbol $R^3$ can also represent a tetrahydro-pyranyl radical, viz. a group of formula (II) wherein both $R^1$ and $R^2$ are taken together and represent a tetramethylene group. In fact $R^3$ is deemed to represent any protecting group of the hydroxy function which is stable in a basic media and easily hydrolysable under acidic conditions.

According to the process of the present invention, the resulting product is then hydrolyzed in the reaction mixture. Said hydrolysis is effected by means of a diluted strong acid of mineral or orgaic origin, or even with water. Suitable acids are sulfuric, phosphoric, hydrochloric, acetic, trichloro-acetic or formic acids e.g. Aqueous sulfuric acid is preferred.

Acidity or basicity and temperature of the reaction mixture determine the nature of the isolated hydrolysis product. When the said hydrolysis is carried out at a temperature inferior or equal to 0° C. and the diluted acid, 10% aqueous $H_2SO_4$ e.g., is added to the alkaline reaction mixture until neutrality only, there is obtained a compound of formula (I) wherein symbol R represents a trialkyl-silyl radical or a group of formula (II). When the said hydrolysis is carried out at a temperature comprised between about 0° and 60° C. and the diluted acid, 35% aqueous $H_2SO_4$ e.g., is added in excess to the reaction mixture, there is obtained the compound of formula (I) wherein symbol R is a hydrogen atom, viz. 4-(1-hydroxy-2,6,6-trimethyl-cyclohex-3-en-1-yl)-but-3-yn-2-ol, having the formula

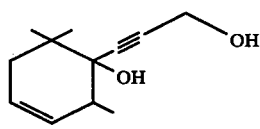
(Ia)

All these acetylenic derivatives can be isolated and purified according to the usual techniques, extraction with organic solvents and fractional distillation e.g.

The above acetylenic derivatives thus prepared are all novel compounds. As examples of such novel compounds, one can cite, in addition to the above mentioned compound of formula (Ia), the compounds of formula (I) wherein symbol R represents a trimethyl-silyl radical, a 3-oxa-pent-2-yl or a tetrahydropyranyl radical.

The organo-metallic derivatives of formula (III) used in the process of the invention can be prepared according to the techniques usual in the art, by the treatment of the corresponding acetylene derivative with the desired metal base, an alkyl-lithium, a potassium alkoxide or an alkyl-magnesium halide e.g.

2,6,6-Trimethyl-cyclohex-3-en-1-one, also used as starting material in the process of the invention, is a novel compound. It can be easily prepared from 2,6,6-trimethyl-cyclohex-2-en-1-one after treatment thereof with an isomerizing agent. To this end, the isomerizing agents cited in the literature can be conveniently used: strong acids possessing an elevated boiling temperature such as p-toluenesulfonic acid (see U.S. Pat. No. 3,385,902), trifluoro-acetic acid or trichloro-acetic acid e.g. Alkali metal alkoxides such as aluminium isopropylate e.g. can also be advantageously used (see U.S. Pat. No. 2,197,462). The interconversion of 2,6,6-trimethyl-cyclohex-2-en-1-one into 2,6,6-trimethyl-cyclohex-3-en-1-one can be carried out at a temperature generally comprised between about 150° and 200° C., preferably of the order of about 190° C.: under these conditions, the formed ketone is directly distilled from the reaction mixture.

Another object of the invention is the use of the above acetylenic derivatives of formula (I) as starting materials for preparing β-damascenone, which use consists in treating the same with an acidic agent. Such a treatment is effected with a strong mineral or organic acid, generally an aqueous solution thereof. Suitable strong mineral acids are for example sulfuric, phosphoric, hydrochloric or perchloric acids; suitable strong organic acids are formic, trichloro-acetic or p-toluenesulfonic acids for example. Good yields of final product can be achieved by using 30 to 40%, preferably 35% aqueous $H_2SO_4$. Although this does not represent a necessary condition, the said acidic treatment can moreover be effected in the presence of an inert solvent such as e.g., dioxane or tetrahydrofuran, or a hydrocarbon, petrol ether for example, or a mixture of hydrocarbons.

The reaction temperature depends on the acidity of the reaction mixture, on the reaction time which is desired to apply and, mainly, on the chemical stability of the reactants involved. The said temperature must be sufficiently high to promote the cleavage of the protecting group of the hydroxy function of the compound of formula (I) (R different from H) and to promote the subsequent interconversion into β-damascenone. The upper limit must correspond to a value where the obtained β-damascenone remains stable in such an acidic medium. The said treatment is generally effected at a temperature comprised between about 60° C. and 100° C., for example of the order of about 70° C. For example, a complete conversion of the compound of formula (I) wherein R is a 3-oxa-pent-2-yl radical into β-damascenone was observed after about 3 hours of a treatment with 35% aqueous $H_2SO_4$ at 70°-72° C.

β-Damascenone, finally, is isolated from the reaction mixture according to the usual techniques, extraction with organic solvents and fractional distillation e.g. With respect to its organoleptic quality, this latter was found in complete accordance with the standards already existing in the perfume and flavour industry.

The invention will be illustrated by the following examples (temperatures given in degrees centigrade).

EXAMPLE 1

2,6,6-Trimethyl-cyclohex-3-en-1-one 150 g of 2,6,6-trimethyl-cyclohex-2-en-1-one and 15 g of aluminium isopropylate were heated at 160° under argon atmosphere until obtention of a clear solution, in a reaction vessel fitted with a fractioning device. The clear mixture was then progressively heated to 190° and kept at this temperature for 60 hours, under vigorous stirring, the formed 2,6,6-trimethyl-cyclohex-3-en-1-one being directly distilled from the reaction mixture. During this period, a further amount of 300 g of starting ketone was added to the reaction mixture. 285 g of a distillate containing 40% of the desired product and 60% of unreacted starting material were thus obtained. After further distillation of the above 285 g there were finally isolated 105 g of the desired ketone having b.p. 62°/15 Torr (yield: 92%—conversion rate of 25%).

IR: 1710, 1680, 685 cm$^{-1}$.

NMR (90 MHz): 1.11 (3H, s); 1.17 (3H, d, J=8 Hz); 1.25 (3H, s); 2.3 (2H, m); 3.04 (1H, m); 5.68 (2H, m) δppm.

MS: M$^+$=138(20); m/e=110(43), 95(87), 82(25), 70(100), 55(15), 42(29), 27(13).

EXAMPLE 2

Compound of formula

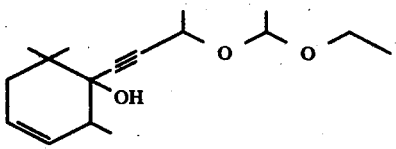

(a) 2-(3-oxa-pent-2-yloxy)-but-3-yne

A mixture of 200 g of but-3-yn-2-ol and 240 g of ethylvinyl ether was added dropwise, at 30° and under nitrogen atmosphere, to 2 g of previously dried KHSO₄. After stirring for 2 hours at 30° the reaction mixture was neutralized with 10 g of Na₂CO₃, then filtered, the organic phase being finally distilled on a VIGREUX column to give 369 g (91% yield) of 2-(3-oxa-pent-2-yloxy)-but-3-yne having b.p. 31°/16 Torr.

IR: 3300, 2100, 1200–1010, 960 cm⁻¹.

NMR (60 MHz): 1.19 (3H,t,J=7 Hz); 1.33 (3H, d, J=6 Hz); 1.44 (3H, d, J=7 Hz); 2.40 (1H, m); 3.56 (2H, m); 4.49 (1H, m); 4.96 (1H, m) δppm.

MS: m/e=127(18), 97(30), 73(67), 53(81), 45(100), 43(37), 27(33).

(b) 55 g of the above compound were added at 23° and under argon atmosphere to a mixture of 75 g of anhydrous diethyl ether and 140 g of ethyl-magnesium bromide 40% in diethyl ether (introduction period: 2h). After heating to reflux for 1 hour, then cooling to 15°, 35 g of 2,6,6-trimethyl-cyclohex-3-en-1-one in 35 ml of anhydrous diethyl ether were added dropwise to the reaction mixture. After cooling to −5° and addition of crushed ice, the reaction mixture was hydrolyzed with 150 ml of 10% aqueous H₂SO₄ and finally extracted with diethyl ether (2×50 ml). After washing of the organic extracts with 5% aqueous NaHCO₃, drying over Na₂SO₄, evaporation and distillation on a VIGREUX column, there were isolated 63.6 g (90% yield) of the desired compound having b.p. 110°–120°/0.03 Torr.

IR: 3500, 1130, 1090, 1050, 960 cm¹.

NMR (60 MHz): signals at 0.9–2.8; 3.3–4.0; 4.2–5.9 δppm.

MS: m/e=212(3), 190(2), 175(4), 166(4), 152(7), 140(12), 125(20), 109(9), 95(27), 81(16), 73(60), 55(22), 45(78), 43(100), 29(44).

(b') To a solution of 5.5 g of the compound prepared according to letter (a) in 7.5 ml of anhydrous diethyl ether there were added dropwise, at 5° and under nitrogen atmosphere, 30 ml of 11% butyl-lithium in hexane. 3.5 g of 2,6,6-trimethyl-cyclohex-3-en-1-one in 3.5 ml of anhydrous diethyl ether were then added at 20° to the above mixture, over a period of 30 minutes. After stirring at room temperature for 2 further hours, the reaction mixture was poured onto crushed ice and extracted with diethyl ether. After drying of the organic layer over Na₂SO₄, evaporation and final distillation on a VIGREUX column, there were isolated 4.6 g (65% yield) of the desired compound.

EXAMPLE 3

Compound of formula

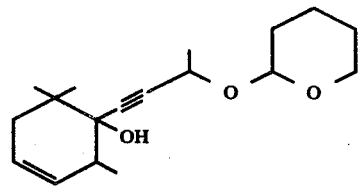

(a) 2-(tetradydropyran-2-yloxy)-but-3-yne

The above compound was prepared in a 97% yield from 70 g of but-3-yn-2-ol, 84 g of 2H-3,4-dihydropyrane and 0.7 g of KHSO₄ in accordance with the method of Example 2 (letter a).

(b) 61.6 g of the above compound were added to 140 g of 40% ethyl-magnesium bromide in diethyl ether as indicated in Example 2 (letter b). 35 g of 2,6,6-trimethyl-cyclohex-3-en-1-one were then added to the organometallic derivative thus obtained to afford, after the above described treatment of extraction and purification, 51.4 g of the desired compound (70% yield) having b.p. 115°–120°/0.02 Torr.

IR: 3460, 1210–960 cm⁻¹.

NMR (60 MHz): signals at 0.9–2.8; 3.2–4.2; 4.3–5.9 δppm.

MS: m/e=224(5), 206(2), 191(8), 175(14), 163(7), 152(39), 140(48), 122(43), 109(34), 96(61), 85(78), 68(74), 55(65), 43(100), 41(96), 29(51).

EXAMPLE 4

Compound of formula

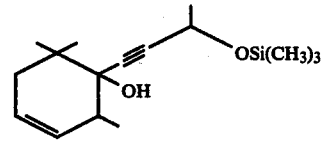

(a) 2-(trimethyl-silyloxy)-but-3-yne

The above compound was prepared in a 60 % yield from 35 g of but-3-yn-2-ol and 50.4 g of trimethylsilyl chloride according to the method given in Can. J. Chem. 43, 2004 (1965); b.p. 117°/760 Torr.

NMR (60 MHz): 0.17 (9H, s); 1.42 (3H, d, J=6 Hz); 2.36 (0.5H, s); 2.39 (0.5H, s); 4.49 (0.5H, q, J=6 Hz); 4.52 (0.5H, q, J=6 Hz) δppm.

MS: m/e=127(100), 101(10), 83(85), 75(22), 73(30), 54(4), 45(17), 27(2).

(b) 5.5 g of the above compound were added to 14 ml of 40% ethyl-magnesium bromide in diethyl ether and 7.5 ml of anhydrous diethyl ether according to the process of Example 2 (letter b). 3.5 g of 2,6,6-trimethyl-cyclohex-3-en-1-one in 3.5 ml of anhydrous diethyl ether were then added to the above reaction mixture, this latter being further stirred for 1 hour. After cooling to −5°, addition of 5 ml of water, subsequent treatments of extraction and drying as described hereinabove and final distillation (110°/0.01 Torr), there were isolated 4.6 g (65% yield) of the desired compound.

IR: 3630, 3500, 1650, 1250, 850, 700 cm⁻¹.

NMR (60 MHz): 0.14 (4.5H, s); 0.17 (4.5H, s); 6.95 (1.5H, s); 1.0 (1.5H, s); 1.11 (3H, s); 1.16 (3H, d, J=7 Hz); 1.38 (1.5H, d, J=7 Hz); 1.42 (1.5H, d, J=7 Hz); 1.6–2.7 (4H, m); 4.52 (0.5H, q, J=7 Hz); 4.56 (0.5H, q, J=7 Hz); 5.1–5.8 (2H, m) δppm.

EXAMPLE 5

4-(1-Hydroxy-2,6,6-trimethyl-cyclohex-3-en-1-yl)-but-3-yn-2-ol 5.5 g of 2-(3-oxa-pent-2-yloxy)-but-3-yne (see Example 2, letter a, 14 ml of 40% ethyl-magnesium bromide in diethyl ether and 3.5 g of 2,6,6-trimethyl-cyclohex-3-en-1-one in anhydrous diethyl ether were reacted as described in Example 2 (letter b). The crude reaction mixture was then acidified with 35% aqueous H$_2$SO$_4$ and stirred during 2 hours at 20°. After addition of 10% aqueous Na$_2$CO$_3$ until neutrality, extraction with diethyl ether, drying of the organic phase over Na$_2$SO$_4$ and evaporation, there were isolated 0.4 g of crude material. This latter was purified by means of crystallization in cyclohexane, m.p. 101°-104°, to give the desired compound.

IR: 3610, 2400, 1210, 1040, 925 cm$^{-1}$.

NMR (90 MHz): 0.98 (1.5H, s); 1.03 (1.5H, s); 1.14 (3H, s); 1.2 (3H, d, J=7 Hz); 1.45 (1.5H, d, J=7 Hz); 1.49 (1.5H, d, J=7 Hz); 1.6-2.0 (3H, m); 2.0-2.6 (2H, m); 4.57 (0.5 H, q, J=7 Hz); 4,61 (0.5H, q, J=7 Hz); 5.2-5.8 (2H, m) δppm.

MS: m/e=190(1), 175(2), 140(100), 125(28), 109(9), 94(44), 79(12), 67(10), 55(12), 43(36), 29(7).

The above compound can also be prepared as indicated hereinafter:

(a) from the compound of Example 2, after treatment thereof at 20° with 35% aqueous H$_2$SO$_4$, in the presence of petrol ether 50/70; or (b) from the compound of Example 4, after treatment thereof at 20° with 10% aqueous H$_2$SO$_4$, in the presence of petrol ether 50/70.

EXAMPLE 6

Preparation of β-damascenone (a) from the compound of Example 2

56 g of the compound prepared according to Example 2, 50 ml of petrol ether 80/100 and 140 ml of 35% aqueous H$_2$SO$_4$ were stirred at 72° for 3 hours, under argon atmosphere. After cooling to room temperature, the organic layer was washed with 2% aqueous NaHCO$_3$ then with water, dried over Na$_2$SO$_4$ and finally evaporated (temperature: lower than 40°; pressure: 15 Torr) to afford 47 g of crude material. After fractional distillation, there were isolated 34.4 g (90% yield) of the desired β-damascenone having a purity of 92%.

After analysis, the thus prepared compound was found identical to a sample of β-damascenone prepared according to Helv. Chim. Acta 53, 541 (1970). The thus prepared compound is perfectly suitable for its use in perfumes or flavours as defined in Swiss Pat. Nos. 520,479 and 509,399 e.g.

(b) from the compound of Example 3

0.6 g of the compound prepared according to Example 3, 10 ml of petrol ether 80/100 and 10 ml of 35% aqueous H$_2$SO$_4$ were stirred at 60° during four days, under argon atmosphere. After the treatments of extraction and purification described hereinabove, β-damascenone was isolated in a 80% yield (purity: 92%).

(c) from the compound of Example 4

4.0 g of the compound prepared according to Example 4, 5 ml of petrol ether 80/100 and 14 ml of 35% aqueous H$_2$SO$_4$ were stirred at 72° for 3 hours under argon atmosphere to afford, after the above treatments of extraction and purification, β-damascenone in a 90% yield (purity: 92%).

(d) from the compound of Example 5

41.6 g of the compound prepared according to Example 5, 50 ml of petrol ether 80/100 and 140 ml of 35% aqueous H$_2$SO$_4$ were stirred at 72° for 3 hours, under argon atmosphere. After extraction and purification as described hereinabove, there were isolated 34.9 g (92% yield) of β-damascenone (purity: 92%).

What I claim is:

1. Process for preparing β-damascenone, which consists essentially of treating a compound of formula

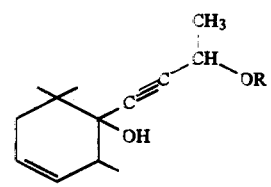
(I)

wherein symbol R represents a hydrogen atom, a trialkylsilyl radical or a group of formula

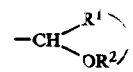
(II)

wherein, when taken separately, each of symbols R$^1$ and R$^2$ represents a lower alkyl radical or, when taken together, R$^1$ and R$^2$ represent a tetramethylene group with an acidic agent.

2. Process according to claim 1, wherein the acidic agent is a diluted strong organic or mineral acid.

3. Process according to claim 1, wherein the treatment is effected at a temperature between about 60° C. and 100° C.

4. Process according to claim 1, wherein the treatment is effected in the presence of an inert organic solvent.

5. Process for preparing β-damascenone, which consists essentially of reacting 2,6,6-trimethyl-cyclohex-3-en-1-one with an organo-metallic derivative having the formula

(III)

wherein symbol ME represents an alkali-metal or a halogen-magnesium radical and R$^3$ represents a trialkylsilyl radical or a group of formula

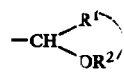
(II)

wherein, when taken separately, each of symbols R$^1$ and R$^2$ represents a lower alkyl radical or, when taken together, R$^1$ and R$^2$ represent a tetramethylene group, subsequently hydrolyzing the obtained reaction product and finally treating the resulting product with an acidic agent.

* * * * *